United States Patent [19]
Shirai

[11] Patent Number: 5,855,556
[45] Date of Patent: Jan. 5, 1999

[54] ULTRASONIC DIAGNOSTIC APPARATUS

[75] Inventor: Takeshi Shirai, Kawasaki, Japan

[73] Assignee: Fujitsu Ltd., Kawasaki, Japan

[21] Appl. No.: 7,147

[22] Filed: Jan. 14, 1998

[30] Foreign Application Priority Data

Sep. 19, 1997 [JP] Japan ..................... 9-255503

[51] Int. Cl.[6] .................................. A61B 8/06
[52] U.S. Cl. .......................... 600/440; 600/455
[58] Field of Search ................... 600/440–441, 600/453–457, 916

[56] References Cited

U.S. PATENT DOCUMENTS 5,474,073  12/1995  Schwartz et al. ................. 600/456
5,722,412   3/1998  Pflugrath et al. ................ 600/459

Primary Examiner—Francis J. Jaworski
Attorney, Agent, or Firm—Staas & Halsey

[57] ABSTRACT

In an ultrasonic diagnostic apparatus, ultrasonic pulse beams are transmitted into an organism, ultrasonic waves reflected within the organism are received to obtain received signals, and an image is displayed in accordance with the received signals thus obtained. The ultrasonic diagnostic apparatus has a blood flow velocity arithmetic unit for extracting a Doppler transition component of the reflected ultrasonic waves in accordance with the received signals to evaluate a distribution of a velocity of a blood flow within the organism in accordance with the extracted Doppler transition component; a blood flow power arithmetic unit for extracting a Doppler transition component of the reflected ultrasonic waves in accordance with the received signals to evaluate a distribution of a power of a blood flow within the organism in accordance with the extracted Doppler transition component; and an image display unit for simultaneously displaying on a display screen a first image representative of a blood flow velocity distribution evaluated by said blood flow velocity arithmetic unit, and a second image representative of a blood flow power distribution evaluated by said blood flow power arithmetic unit.

4 Claims, 4 Drawing Sheets

ULTRASONIC DIAGNOSTIC APPARATUS

BACKGROUND OF THE INVENTION

1. Field of the Invention

The present invention relates to an ultrasonic diagnostic apparatus in which ultrasonic pulse beams are transmitted into an organism, ultrasonic waves reflected within the organism are received to obtain received signals, and an image is displayed in accordance with the received signals thus obtained.

2. Description of the Related Art

Hitherto, there has been widely used for the purpose of diagnoses of a disease inside an organism, particularly, the human body an ultrasonic diagnostic apparatus in which ultrasonic waves are transmitted into the organism, and the ultrasonic waves reflected at tissues within the organism are received to obtain received signals, so that an image is produced in accordance with the received signals thus obtained.

As one of functions incorporated into such an ultrasonic diagnostic apparatus, there is known a so-called color-Doppler mode in which there is utilized such a Doppler phenomenon that when an ultrasonic wave is reflected on a blood flow within the subject, the reflected ultrasonic wave undergoes a frequency transition according to a direction of the blood flow and a velocity of the blood flow, components, which undergo a frequency transition, of the reflected ultrasonic wave are extracted to detect a direction and a velocity of the blood flow on the respective point, and a tomographic image (a color-Doppler image) wherein for example, a blood flow involved in a direction coming to an ultrasonic probe serving for transmission and reception of ultrasonic waves, a blood flow involved in a direction going away from the ultrasonic probe, and a velocity of a blood flow are represented by red, blue and luminance, respectively, is displayed.

Further, there is also known a so-called power-Doppler mode. As mentioned above, according to the color-Doppler mode, components, which undergo a frequency transition, of the reflected ultrasonic wave are extracted to detect a direction and a velocity of the blood flow on the respective point. On the other hand, according to the power-Doppler mode, components, which undergo a frequency transition, of the reflected ultrasonic wave are extracted to detect a power of the component undergoing the frequency transition on each of points within the tomographic plane, and a tomographic image (a power-Doppler image) wherein the magnitude of the power is represented by luminance or colors, is displayed. The power-Doppler image has, as compared with the color-Doppler image, an aspect that while it is unclear as to velocity and directions of a blood flow, it is displayed with more favorable S/N as to existence of a blood flow.

Hitherto, in the color-Doppler mode, it is used in such a manner that for example, two color-Doppler images are put side by side, and as one of those two images an image at a certain time point (a certain one frame of image) is displayed on a stationary basis (it is referred to as a "freezing" that a certain one frame of image is continued to display, and the image displayed in this manner is referred to as a "freeze image"), and as another of those two images an image representative of a blood flow distribution is displayed on a real time basis. The color-Doppler mode is mainly used for a diagnosis of a heart.

In view of the fact that recently performances of the color-Doppler mode and the power-Doppler mode are improved, those modes are becoming used also for a diagnosis of the abdominal region which abounds in faint blood flows as compared with the heart. An important matter of concern in a diagnosis of the abdomen is the presence of a tumor in the abdomen and the presence of blood flows flowing inside the tumor. As mentioned above, as to drawing the presence of a blood flow per se, the power-Doppler mode is more excellent as compared with the color-Doppler mode, and is becoming noticed. However, when it is required to make a closer diagnosis, it is also important to grasp the behavior of the blood flows flowing inside the tumor, that is, a blood direction, a blood velocity and their variations in time. The power-Doppler image involves no information as to those messages. Thus, in order to obtain information as to those messages, it is obliged to utilize the color-Doppler image even if it is poor in S/N ratio.

For example, even if it is intended that the power-Doppler mode is selected beforehand to identify on the power-Doppler image the presence of the blood flow inside the tumor, and then the mode is switched to the color-Doppler mode to identify on the color-Doppler image directions and velocity of the blood flow inside the tumor, it happens that even if the presence of the blood flow inside the tumor can be identified on the power-Doppler image, it is difficult after changeover to the color-Doppler mode to identify the associated blood flow on the color-Doppler image, since the blood flow of interest is originally an extremely fine blood flow, and a quantity of blood flowing therethrough is small, and in addition the color-Doppler image involves a poor S/N ratio.

SUMMARY OF THE INVENTION

In view of the foregoing, it is therefore an object of the present invention to provide an ultrasonic diagnostic apparatus having a function of facilitating it to establish the mapping between a location on the power-Doppler image and a location on the color-Doppler image.

To achieve the above-mentioned objects, according to the present invention, there is provided an ultrasonic diagnostic apparatus in which an ultrasonic pulse beam is transmitted into an organism and ultrasonic waves reflected within the organism are received to obtain received signals, this process is repeatedly performed to obtain the received signals, and an image is displayed in accordance with the received signals thus obtained, said ultrasonic diagnostic apparatus comprising:

a blood flow velocity arithmetic unit for extracting a Doppler transition component of the reflected ultrasonic waves in accordance with the received signals to evaluate a distribution of a velocity of a blood flow within the organism in accordance with the extracted Doppler transition component;

a blood flow power arithmetic unit for extracting a Doppler transition component of the reflected ultrasonic waves in accordance with the received signals to evaluate a distribution of a power of a blood flow within the organism in accordance with the extracted Doppler transition component; and an image display unit for simultaneously displaying on a display screen a first image representative of a blood flow velocity distribution evaluated by said blood flow velocity arithmetic unit, and a second image representative of a blood flow power distribution evaluated by said blood flow power arithmetic unit.

According to the ultrasonic diagnostic apparatus of the present invention, so-called color Doppler image and power Doppler image are simultaneously displayed on a one display screen. This feature makes it possible to readily recognize the associated points between these two types of images, and thus, for example, it is possible to identify the existence of a blood flow within a tumor on the power Doppler image, and also to identify a direction and a velocity of the blood flow thus identified on the color Doppler image.

In the ultrasonic diagnostic apparatus as mentioned above, it is preferable that the ultrasonic diagnostic apparatus further comprises a display control unit adapted to provide, independently for said first image and said second image, a selective control between a dynamic image display mode in which a plurality of frames of images, which are sequentially generated, are sequentially transmitted to said image display unit so that the plurality of frames of images are sequentially displayed on the display screen, and a still image display mode in which a frame of image is kept on being displayed on the display screen.

An arrangement, in which the color Doppler image and power Doppler image are allowed to independently be frozen or released from the freezing, implement an ultrasonic diagnostic apparatus which is excellent in operability and is more useful for diagnoses.

Further, in the ultrasonic diagnostic apparatus as mentioned above, it is preferable that the ultrasonic diagnostic apparatus further comprises a display control unit adapted to provide, for said first image and said second image, a selective control between a dynamic image display mode in which a plurality of frames of images, which are sequentially generated on one of said first image and said second image, are sequentially transmitted to said image display unit so that the plurality of frames of images are sequentially displayed on the display screen, and a still image display mode in which a frame of image, on another of said first image and said second image, is kept on being displayed on the display screen.

When it is permitted that either one of the color Doppler image and the power Doppler image, at the same time, is in the state of freezing, it is possible to meet the conditions of ultrasonic transmission and reception and the conditions of filtering to an image which is displayed in a dynamic picture image.

Furthermore, in the ultrasonic diagnostic apparatus as mentioned above, it is preferable that the ultrasonic diagnostic apparatus further comprises a map storage unit for storing a first map for defining an association between a blood flow velocity data representative of the blood flow velocity distribution and a display data representative of the first image displayed on the display screen of said image display unit, and a second map for defining an association between a blood flow power data representative of the blood flow power distribution and a display data representative of the second image displayed on the display screen of said image display unit, said second map being different from said first map.

It is acceptable that a map for the color Doppler image and a map for the power Doppler image are used on a common basis. In this case, however, the color Doppler image and the power Doppler image may be displayed with the similar color and thus it apparently hard to discriminate between the color Doppler image and the power Doppler image. For this reason, the color Doppler image and the power Doppler image are sorted by a display map. This feature makes it possible to display images with colors and luminance suitable for the respective ones thereby obtaining images easy to see.

DESCRIPTION OF THE PREFERRED EMBODIMENTS

Hereinafter, there will be described embodiments of the present invention.

Figure 1:
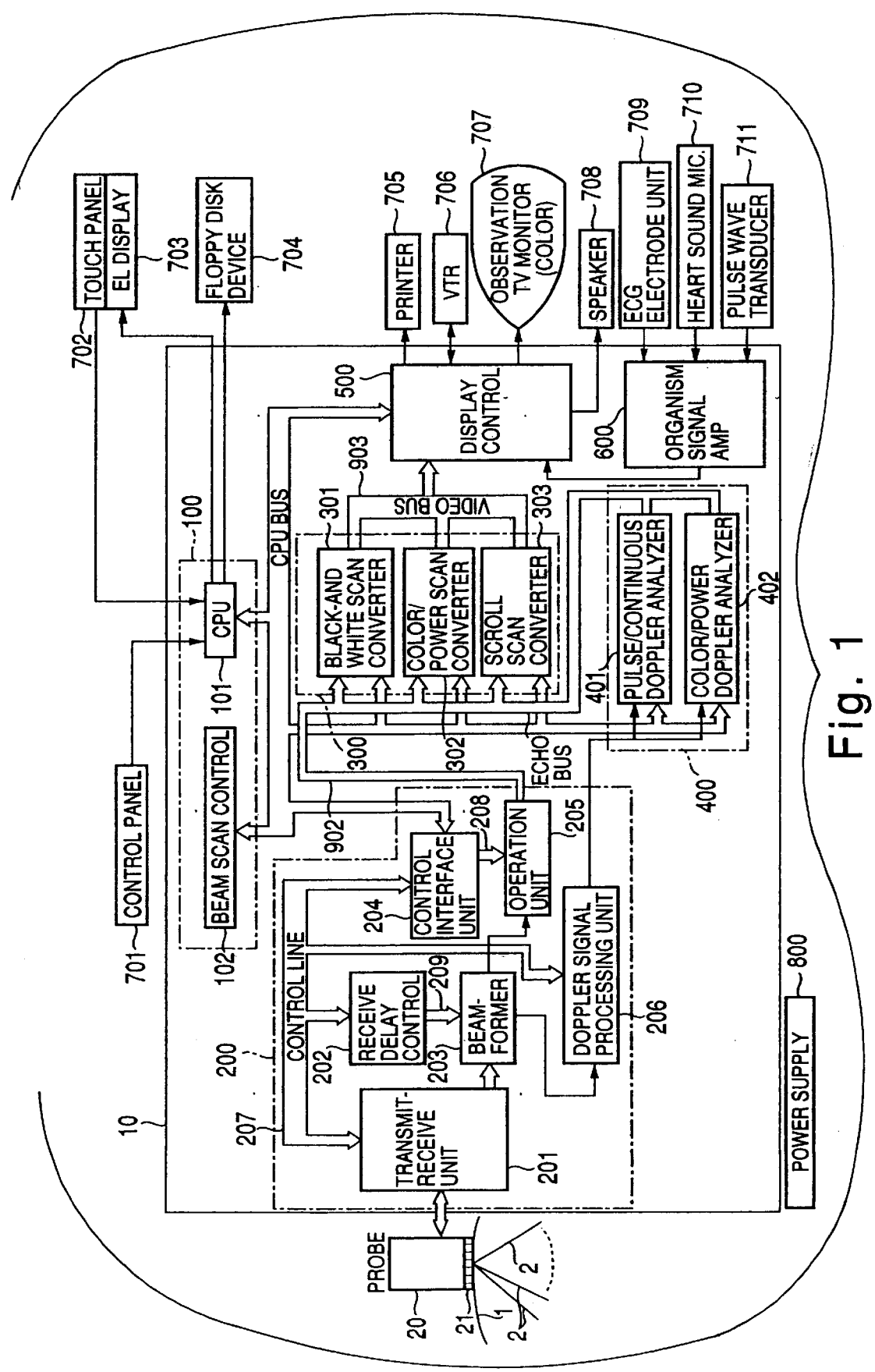
FIG. 1 is a block diagram of an ultrasonic diagnostic apparatus according to an embodiment of the present invention.

FIG. 1 is a block diagram of an ultrasonic diagnostic apparatus according to an embodiment of the present invention. There will be described an outline of the ultrasonic diagnostic apparatus referring to this block diagram.

First, there will be described a structure of the ultrasonic diagnostic apparatus hereinafter.

A main frame 10 of the ultrasonic diagnostic apparatus comprises a control unit 100, a signal processing unit 200, a digital scan converter unit 300, a Doppler processing unit 400, a display control unit 500 and an organism signal amplifier unit 600. The control unit 100 comprises a CPU 101 and a beam scan control unit 102. Connected to the CPU 101 are a control panel 701, a unitary body of touch panel 702 and EL display 703, and a floppy disk device 704.

The signal processing unit 200 comprises a transmit-receive unit 201, a receive delay control unit 202, a beamformer unit 203, a control interface unit 204, an operation unit 205 and a Doppler signal processing unit 206. The control interface unit 204, the transmit-receive unit 201, the receive delay control unit 202, and the Doppler signal processing unit 206 are connected to one another via a control line 207. Further, the control interface unit 204 is connected via a control line 208 to the operation unit 205. The receive delay control unit 202 and the beamformer unit 203 are connected to one another via a control line 209. Detachably connected to the transmit-receive unit 201, which constitutes the signal processing unit 200, is an ultrasonic probe 20, by the maximum, four pieces of ultrasonic probe 20.

The digital scan converter unit 300 comprises a black-and-white scan converter 301, a color/power scan converter 302 and a scroll scan converter 303.

The Doppler processing unit 400 comprises a pulse/continuous wave Doppler analyzing unit 401 and a color Doppler analyzing unit 402.

The display control unit 500 is illustrated with a single block. Connected to the display control unit 500 are a printer 705, a VTR (Video Tape Recorder) 706, an observation television monitor 707 and a speaker 708.

The organism signal amplifier unit 600 is also illustrated with a single block. Connected with the organism signal amplifier unit 600 are an ECG electrode unit 709, a heart sound microphone 710 and a pulse wave transducer 711.

The ultrasonic diagnostic apparatus further comprises a power source unit 800 connected to a commercial power supply for supplying necessary power to individual sections of the ultrasonic diagnostic apparatus.

The main frame 10 has a CPU bus 901 for connecting the CPU 101 and the beam scan control unit 102, which constitute the control unit 100, the control interface unit 204, which constitutes the signal processing unit 200, the black-and-white scan converter 301, the color/power scan converter 302 and the scroll scan converter 303, which constitute the digital scan converter unit 300, the pulse/continuous wave Doppler analyzing unit 401 and the color/power Doppler analyzing unit 402, which constitute the Doppler processing unit 400, and the display control unit 500 with each other. The main frame 10 further has an echo bus 902 for supplying image data generated from the operation unit 205, which constitutes the signal processing unit 200, to the digital scan converter unit 300. With respect to data generated from the pulse/continuous wave Doppler analyzing unit 401 and the color/power Doppler analyzing unit 402, which constitute the Doppler processing unit 400, such data are also supplied through the echo bus 902 to the digital scan converter unit 300. The main frame 10 further has a video bus 903 for transmitting a video signal generated from anyone of the black-and-white scan converter 301, the color/power scan converter 302 and the scroll scan converter 303, which constitute the digital scan converter unit 300, to the display control unit 500.

The control panel 701 consists of a keyboard, etc. having a number of keys arranged. When the control panel 701 is operated, operation information is detected by the CPU 101, so that an instruction associated with the operation information is transmitted to the beam scan control unit 102, the control interface unit 204, the digital scan converter unit 300, or the display control unit 500 in accordance with the the instruction.

The EL display unit 703 has a liquid-crystal display screen. The CPU 101 serves as an EL line drawing generating unit for generating an EL line drawing to be displayed on the liquid-crystal display screen of the EL display unit 703, too. The EL line drawing generated in the CPU 101 is displayed on the liquid-crystal display screen of the EL display unit 703. The liquid-crystal display screen of the EL display unit 703 is provided with the touch panel 702. When an operator touches the touch panel 702 by his fingers, position information representative of the associated touched position on the touch panel 702 is transmitted to the CPU 101. The touch panel 702 and the EL display unit 703 are arranged, so that various types of instructions to the ultrasonic diagnostic apparatus can be readily inputted, in such a manner that, for instance, when it is instructed to the ultrasonic diagnostic apparatus through an operation of the control panel 701 that a parameter as to a certain mode is set up for the ultrasonic diagnostic apparatus, the CPU 101 causes the EL display unit 703 to display a table of a number of parameters to be set up for the selected mode, so that an operator touches the touch panel 702 by his fingers to set up a desired parameter.

The floppy disk device 704 is a device onto which a floppy disk (not illustrated) is detachably loaded, wherein the loaded floppy disk is accessed. The CPU 101 causes instructions made by an operator through an operation of the control panel 701 and the touch panel 702 to be written into the floppy disk loaded onto the floppy disk device 704. When the power supply of the ultrasonic diagnostic apparatus is turned on, or when a reset to the initial state is instructed through an operation of the control panel 701, various types of instruction information, which are stored in the floppy disk device 704 loaded onto the floppy disk device 704, are read out therefrom and fed to the CPU 101 so that the CPU 101 sets up the individual sections of the ultrasonic diagnostic apparatus to the initial state in accordance with the instruction information. There will exist a number of parameters to be set up by an operator through an operation of the control panel 701 and the touch panel 702, which are needed when the ultrasonic diagnostic apparatus is operated. It will be very troublesome for the operator to do over again a setting of such a number of parameters, for example, whenever the power supply turns on. For this reason, parameters of the initial state, etc. are written in the floppy disk beforehand, and when the power supply of the ultrasonic diagnostic apparatus is turned on, or when a reset to the initial state is instructed, the parameters and the like stored in the floppy disk are read out therefrom to set up the individual sections of the ultrasonic diagnostic apparatus in accordance with the parameters and the like thus read, thereby contributing to an enhancement of efficiency in setting the parameters and the like.

The CPU 101, which constitutes the control unit 100, mainly serves as a man-machine interface, as mentioned above. On the other hand, the beam scan control unit 102, which also constitutes the control unit 100, is mainly in charge of the control, for example, of timing of transmit and receive of ultrasonic waves in the ultrasonic diagnostic apparatus, which needs an operational ability on a real-time basis. According to this type of ultrasonic diagnostic apparatus, when transmit and receive of ultrasonic waves are performed, data for controlling the individual sections constituting the signal processing unit 200 are transmitted from the beam scan control unit 102 through the CPU bus 901 to the control interface unit 204, so that the control interface unit 204 controls via a control line 207 the transmit-receive unit 201, the receive delay control unit 202, and the Doppler signal processing unit 206. Further, the control interface unit 204 controls via a control line 208 the operation unit 205. The receive delay control unit 202 controls the beamformer unit 203 via the control line 209 under control of the control interface unit 204.

The transmit-receive unit 201 is coupled to the ultrasonic probe 20. With respect to the ultrasonic probe, there exist, for example, a linear scan type of ultrasonic probe, a convex scan type of ultrasonic probe, and a sector scan type of ultrasonic probe. As an especial type of ultrasonic probe, there is a type of ultrasonic probe to be inserted into a body cavity. Further, with respect to those various types of ultrasonic probes, there exist many types of ultrasonic probes, which may be classified in accordance with a difference in frequency of the ultrasonic waves to be used. In order that a ultrasonic probe is loaded on the main frame 10, a connector (not illustrated) is used. The main frame 10 end is provided with four connectors adapted to be connected to ultrasonic probes. Thus, as mentioned above, it is possible to simultaneously load onto the connectors the ultrasonic probes, by the maximum 4 pieces, of the above-mentioned various types of ultrasonic probes. When a ultrasonic probe is loaded on the main frame 10, the main frame 10 may identify information as to which type of ultrasonic prob is loaded. Such information is transmitted via the control line 207, the control interface unit 204 and the CPU bus 901 to the CPU 101. On the other hand, the control panel 701 issues an instruction as to which ultrasonic probe is to be used among the ultrasonic probes connected to four connectors of the main frame 10 end, when the ultrasonic diagnostic apparatus is used. Such an instruction is transferred via the CPU bus 901 to the beam scan control unit 102, and data according to the ultrasonic probe to be used is transmitted via the CPU bus 901, the control interface unit 204 and the control line 207 to the transmit-receive unit 201. Upon receipt of such data, the transmit-receive unit 201 transmits high voltage pulses (which will be described latter) to the ultrasonic probe 20 thus indicated to generate ultrasonic waves, and receives signals which are received by the ultrasonic probe 20. Here, it is assumed that the ultrasonic probe 20, as shown in FIG. 1 by one, is selected for transmission and reception of ultrasonic waves.

The ultrasonic probe 20 shown in FIG. 1 is a so-called sector scanning type of ultrasonic probe. On the tip of the ultrasonic probe 20, there are arranged a plurality of ultrasonic transducers 21, which are put to a surface of the organism 1 (particularly human body) to transmit and receive ultrasonic waves. In this condition, high voltage pulses for transmission and reception of ultrasonic waves are applied from the transmit-receive unit 201 to the plurality of ultrasonic transducers 21, respectively. The high voltage pulses applied to the plurality of ultrasonic transducers 21 are controlled in a relative time difference under control of the control interface unit 204. Ultrasonic pulse beams are transmitted from the plurality of ultrasonic transducers 21 along anyone of a plurality of scan lines 2 extending to the inside of the organism 1 in such a manner that the focus of the ultrasonic pulse beams is adjusted on a predetermined depth position inside of the organism 1 in accordance with a control of the relative time difference as to the application of the high voltage pulses to the plurality of ultrasonic transducers 21.

The attribute of the ultrasonic pulse beam to be transmitted, that is, a direction of the ultrasonic pulse beam, a depth position of the focus, a central frequency and the like, is determined in accordance with control data transferred from the beam scan control unit 102 via the CPU bus 901 to the control interface unit 204.

The ultrasonic pulse beam is reflected on the individual points on the one scan line during travelling inside the organism 1, and returns to the ultrasonic probe 20 so that the reflected ultrasonic waves are received by the plurality of ultrasonic transducers 21. A plurality of received signals, which are obtained through receiving the reflected ultrasonic waves, are supplied to the transmit-receive unit 201 so as to be amplified by a plurality of preamplifiers (not illustrated) of the transmit-receive unit 201, and then fed to the beamformer unit 203. The beamformer unit 203 is provided with an analog delay line having a number of center taps. The center taps are selected in operation to receive the plurality of received signals transmitted from the transmit-receive unit 201 in accordance with a control of the receive delay control unit 202, whereby the plurality of received signals are relatively delayed and added together in current. Controlling a relative delay pattern as to the plurality of received signals may emphasize the reflected ultrasonic waves in the direction along the scan line identical with the scan line associated with the time of the ultrasonic wave transmission, and forms a so-called reception ultrasonic beam in which the focus of the ultrasonic pulse beams is adjusted on a predetermined depth position inside of the organism 1. Since ultrasonic waves travel slowly inside of the organism 1 as compared with a rate of the signal processing, it is possible to implement a so-called dynamic focus in which the focus is sequentially shifted to the deeper position inside of the subject while receiving the ultrasonic waves along one scan line. In this case, the center taps of the analog delay line are switchingly selected by the receive delay control unit 202 in response to the signals sequentially obtained by the ultrasonic transducers, even during once receiving associated with once transmitting the ultrasonic pulse beam.

The attribute of the reception ultrasonic beam, that is, a direction of the reception ultrasonic beam, a depth position of the focus and the like, is also determined in accordance with control data which is transferred from the beam scan control unit 102 via the CPU bus 901 to the control interface unit 204, and further transferred via the control line 207 to the receive delay control unit 202. The receive delay control unit 202 controls the beamformer unit 203 in accordance with the control data thus transferred.

According to the above-mentioned explanation, the high voltage pulses are applied to the ultrasonic transducers 21 to transmit the ultrasonic pulse beam. In this case, as mentioned above, since ultrasonic waves travel slowly inside of the organism as compared with a rate of the signal processing, it is possible, through measuring time from a starting time of application of the high voltage pulses to the ultrasonic transducers 21 to a time of receive of the reflected ultrasonic waves by the ultrasonic transducers 21, to identify the signal obtained at that time concerned with receiving of the reflected ultrasonic waves with respect to the association of the reflected ultrasonic wave with the depth position inside of the organism. That is, the feature that the ultrasonic wave to be transmitted is shaped as a pulse may provide a resolution with respect to the depth direction of the organism. Usually, in this manner, the high voltage pulses are applied to the ultrasonic transducers 21. In the special case, however, on condition that it is permitted to have no resolution with respect to the depth direction of the organism , it happens that a continuously repetitive high voltage pulse train signal is applied to the ultrasonic transducers 21 to transmit ultrasonic beams in the form of a continuous wave.

Also hereinafter, the ultrasonic diagnostic apparatus will be explained on the assumption that a pulse-like shaped ultrasonic beam is transmitted, except for a case that when the pulse/continuous wave Doppler analyzing unit 401, which constitutes the Doppler processing unit 400, is explained, the continuous wave is referred to.

In the manner as mentioned above, the transmit-receive unit 201 and the beamformer unit 203 sequentially repeatedly perform transmission and reception of the ultrasonic pulse beams along each of a plurality of scanning lines 2 inside of the organism 1, so that received signals thus generated, each representative of the reception ultrasonic beam along each of the scanning lines, are sequentially fed to the operation unit 205. In the operation unit 205, the received signals are subjected to logarithmic compression, detection, and filtering processings, etc. according to a designation issued through operation of the control panel 701 as to which depth area inside of the organism 1 an image is to be displayed concerned with, that is, a designation as to whether it is sufficient that an image concerned with only the shallow area inside of the organism 1 is displayed, or a designation as to what degree of depth area an image is to be displayed concerned with. The analog received signals thus processed are converted into digital received signals by an A/D converter unit, and the digital received signals thus converted are outputted form the operation unit 205. The received signals outputted from the operation unit 205 are fed via the echo bus 902 to the black-and-white scan converter 301, which constitutes the digital scan converter unit 300. The black-and-white scan converter 301 practices an interpolation processing to produce data associated with the respective pixels for a display, and then transmits the data thus produced for a display via the video bus 903 to the display control unit 500. The display control unit 500 causes the observation television monitor 707 to display a B-mode image caused by the ultrasonic reflection intensity distribution on the tomographic plane of the organism defined by a plurality of scan lines 2. At that time, if necessary, it is possible to display patient's names, photographing date, photographing conditions, etc. superimposing on the B-mode image. The display control unit 500 has a frame memory. As the B-mode image, when the frame memory is sequentially rewritten, it is possible to display a dynamic image representative of the state in which the inside of the organism 1 moves, alternatively when the frame memory is stopped in rewriting, it is possible to display a static image (freeze image) at a certain time. Further, when a timing of rewriting of the frame memory is controlled, it is possible to display an image in a certain phase of a movement of the heart of an organism, which is synchronized with the movement of the heart, in accordance with a synchronizing signal generated from the organism signal amplifier unit 600.

Connected to the organism signal amplifier unit 600 are the ECG electrode unit 709, the heart sound microphone 710 and the pulse wave transducer 711. The organism signal amplifier unit 600 generates the synchronizing signal in accordance with any one of these elements or a plurality of sensors, and transmits the same to the display control unit 500.

Connected to the display control unit 500 are the observation television monitor 707, and the printer 705 and the VTR (Video Tape Recorder) 706 as well. The display control unit 500 outputs images displayed on the observation television monitor 707 to the printer 705 or the VTR 706 in accordance with an instruction from an operator.

Again, an explanation will be continued from the signal processing unit 200.

When it is desired to know time variation of information as to the reflection of ultrasonic waves on a certain one scan line extending to the inside of the organism, the ultrasonic waves are repeatedly transmitted and received along a certain one scan line of interest, and data representative of the reception ultrasonic beam of the organism along the one scan line is transmitted via the echo bus 902 to the scroll scan converter 303. The scroll scan converter 303 generates a video signal representative of an image (an M-mode image) in which the ultrasonic reflection intensity distribution in the depth direction of the organism along the one scan line is given in the longitudinal direction, and the lateral axis consists of a time axis, wherein the image is scrolled in the time axis direction. The video signal thus generated is fed via the video bus 903 to the display control unit 500, so that an image based on the video signal is displayed, for example, on the observation television monitor 707.

The display control unit 500 has a function such that the video signal representative of the B-mode image transmitted from the black-and-white scan converter 301 and the video signal representative of the M-mode image transmitted from the scroll scan converter 303 are arranged side by side, and in addition a function such that a color Doppler image, or a power Doppler image, which will be described later, is superposed on the B-mode image. The observation television monitor 707 is adapted to display thereon a plurality of images being arranged side by side in accordance with an instruction from an operator, alternatively display a plurality of images being superposed.

Again, returning to the explanation of the analog processing unit 200, the Doppler signal processing unit 206, which constitutes the signal processing unit 200, serves as a structure element for determining a blood flow distribution of the inside of the organism 1, or a blood flow distribution at a certain point or on a certain one scan line. In the Doppler signal processing unit 206, a received signal representative of the reception ultrasonic beam generated in the beamformer unit 203 is subjected to a so-called quadrature detection and in addition converted into digital data through an A/D conversion. The data, which has been subjected to the quadrature detection, is outputted from the Doppler signal processing unit 206, is fed to the Doppler processing unit 400. The Doppler processing unit 400 comprises the pulse/continuous wave Doppler analyzing unit 401 and the color/power Doppler analyzing unit 402. Here, it is assumed that the data outputted from the Doppler signal processing unit 206 is fed to the color Doppler analyzing unit 402. The color/power Doppler analyzing unit 402 determines data representative of a blood flow distribution on an area of interest (ROI) on the B-mode image, which is designated by an operator, by an auto-correlation operation based on data obtained through performing, for example, eight times of ultrasonic transmit and receive on each scan line. The data representative of a blood flow distribution on the area (ROI) is fed via the echo bus 902 to the color/power scan converter 302. The color/power scan converter 302 converts the data representative of a blood flow distribution on the area (ROI) into data having display pixels, and transmits the data via the video bus 903 to the display control unit 500. The display control unit 500 superimposes, in case of the blood flow distribution, a color Doppler image, in which a blood in a direction coming near the ultrasonic probe 20, a blood in a direction going away from the ultrasonic probe 20, and a blood flow velocity are represented by, for example, red, blue and luminance, respectively, on the area (ROI) of the B-mode image transmitted from the black-and-white scan converter 301, and causes those images to be displayed on the observation television monitor 707. Thus, it is possible to grasp the outline of the blood flow distribution on the area (ROI). In a similar way, it is possible to superimpose a power Doppler image representative of a blood flow distribution on the area (ROI) of the B-mode image and display the synthesized images.

When an operator inputs a requirement to observe in detail a blood at a certain one point on the area (ROI) or on a certain one scan line, then the transmit-receive unit 201 repeats a lot of number of times of transmit and receive of the ultrasonic waves in a direction along a one scan line passing through the one point of interest, or a direction along the one scan line of interest. And data, which is generated in the the Doppler signal processing unit 206 in accordance with the signals thus obtained by the repetitive transmit and receive of the ultrasonic waves, is fed to the pulse/continuous wave Doppler analyzing unit 401 constituting the Doppler processing unit 400. When it is interested in the a blood flow at a certain point within an organism, a pulse-like shaped ultrasonic beam is transmitted into the organism. On the other hand, when it is desired to obtain blood information excellent in S/N ratio, permitting that blood information on a certain one scan line is averaged, a ultrasonic beam is transmitted in the form of a continuous wave into the organism.

The pulse/continuous wave Doppler analyzing unit 401 performs an FFT (Fast Fourier Transform) operation based on data obtained through carrying out a lot of number of times of transmit and receive of the ultrasonic waves on a certain one point, or a certain one scan line to obtain blood flow information on the one point, or blood flow information averaged on the one scan line. Data representative of the blood flow information obtained in the pulse/continuous wave Doppler analyzing unit 401 is fed via the echo bus 902 to the scroll scan converter 303. The scroll scan converter 303 generates data representative of an image in which the longitudinal axis and the lateral axis denote a blood flow velocity and a time axis, respectively, and the image may scroll in a direction of the time axis. This data is fed via the video bus 903 to the display control unit 500. The display control unit 500 causes the video signal to be displayed on the observation television monitor 707 together with the B-mode image transmitted from the black-and-white scan converter 301, for example.

Figure 2:
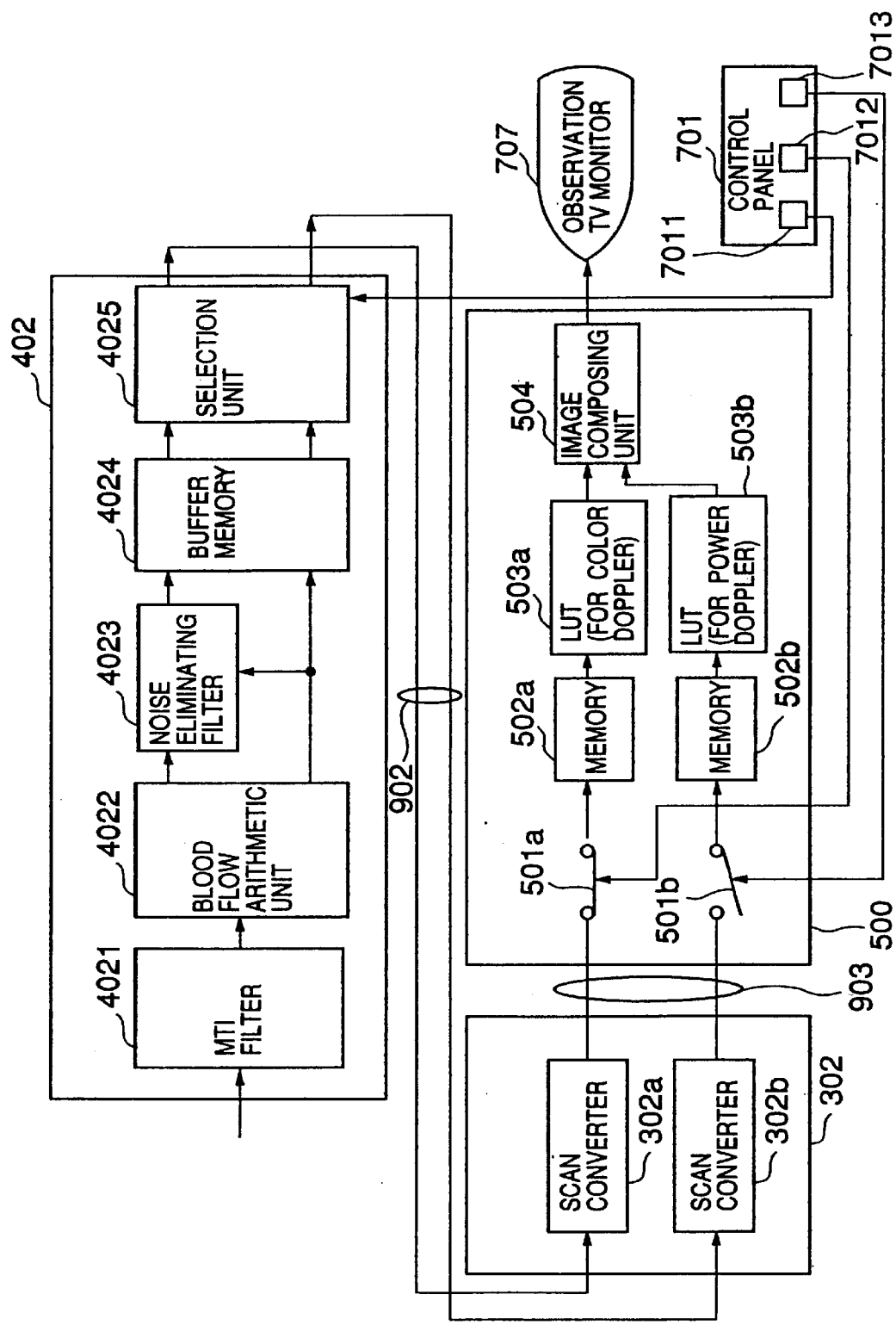
FIG. 2 is a detail block diagram of characteristic portions of the ultrasonic diagnostic apparatus according to the embodiment of the present invention.

FIG. 2 is a detail block diagram of characteristic portions of the ultrasonic diagnostic apparatus according to the embodiment of the present invention.

As mentioned above, in the Doppler signal processing unit 206 constituting the signal processing unit 200, a received signal representative of the reception ultrasonic beam generated in the beamformer unit 203 is subjected to a so-called quadrature detection and in addition converted into digital data through an A/D conversion. The data after the quadrature detection is fed to an MIT filter 4021 of the color/power Doppler analyzing unit 402. The MIT filter 4021 is suitable for eliminating a component as to a very slow movement of tissues within an organism and extracting only a blood flow component.

Data, in which only the blood flow component is extracted, is fed to a blood flow arithmetic unit 4022 for evaluating a blood flow velocity distribution and a blood flow power distribution on the basis of the data thus fed. Color Doppler data representative of the blood flow velocity distribution is supplied to a buffer memory 4024 after eliminating by a noise eliminating filter 4023 data on a region in which power Doppler data representative of the blood flow power distribution does not exist or no blood vessel exists. The noise eliminating filter 4023 is intended to eliminate color Doppler data on a region in which it is determined that no blood vessel exists, since the color Doppler data is poor in S/N ratio.

A selection unit 4025 selectively outputs either one or both of color Doppler data and power Doppler data in accordance with a mode selection control signal designated through a mode selection button 7011 of an operation panel 701. The color Doppler data or power Doppler data derived from the selection unit 4025 is outputted from the color/power Doppler analyzing unit 402. The color Doppler data or power Doppler data outputted from the color/power Doppler analyzing unit 402 is fed via the echo bus 902 to the color/power scan converter 302.

The color/power scan converter 302 comprises a color scan converter 302*a* and a power scan converter 302*b*. The color scan converter 302*a* and the power scan converter 302*b* convert the color Doppler data and the power Doppler data into color Doppler data and power Doppler data having pixels for a display, respectively. The color Doppler data and the power Doppler data produced in the color/power scan converter 302 are fed via the video bus 903 to the display control unit 500.

The display control unit 500 comprises a color Doppler freeze switch 501*a*, a power Doppler freeze switch 501*b*, a color Doppler LUT (Look-Up Table) 503*a*, a power Doppler LUT 503*b*, and an image composing unit 504. The color Doppler freeze switch 501*a* and the power Doppler freeze switch 501*b* provided on the control panel 701 are controlled in turn-on and off by a color Doppler freeze selection button 7012 and a power Doppler freeze selection button 7013, respectively.

When the color Doppler freeze switch 501*a* is turned on, the color Doppler data, which is fed via the video bus 903 to the display control unit 500, is fed via the color Doppler freeze switch 501*a* to a color Doppler memory 502*a*. The color Doppler memory 502*a* is rewritten into a new color Doppler data for each frame. In this case, as will be described later, a dynamic picture image of the color Doppler image is displayed on the observation television monitor 707. When the color Doppler freeze switch 501*a* is switched from the turn-on state to the turn-off state, the color Doppler memory 502*a* maintains the state that the color Doppler data, which is involved in the frame immediately before the color Doppler freeze switch 501*a* is switched to the turn-off state, is stored. In this case, a freeze image of the color Doppler image is displayed on the observation television monitor 707.

This is the similar as to the matter of the power Doppler data. When the power Doppler freeze switch 501*b* is turned on, the power Doppler data, which is fed via the video bus 903 to the display control unit 500, is fed via the power Doppler freeze switch 501*b* to a power Doppler memory 502*b*. The power Doppler memory 502*b* is rewritten into a new power Doppler data for each frame. In this case, a dynamic picture image of the power Doppler image is displayed on the observation television monitor 707. When the power Doppler freeze switch 501*b* is switched from the turn-on state to the turn-off state, the power Doppler memory 502*b* maintains the state that the power Doppler data, which is involved in the frame immediately before the power Doppler freeze switch 501*b* is switched to the turn-off state, is stored. In this case, a freeze image of the power Doppler image is displayed on the observation television monitor 707.

The color Doppler data and the power Doppler data, which are stored in the color Doppler memory 502*a* and the power Doppler memory 502*b*, respectively, are read out from the color Doppler memory 502*a* and the power Doppler memory 502*b*, respectively, and referring to the color Doppler LUT 503*a* and the power Doppler LUT 503*b*, respectively, are converted into data for a display. According to the present embodiment, since the look-up tables are individually prepared for the color Doppler and the power Doppler, it is possible to obtain images displayed in color and luminance suitable for the color Doppler image and the power Doppler image.

The respective data for a display, which are obtained through the color Doppler LUT 503*a* and the power Doppler LUT 503*b*, are supplied to the image composing unit 504 in which as will be described referring to FIG. 3, a field of image, in which the color Doppler image and the power Doppler image are put side by side, is formed. Incidentally, the image composing unit 504 may perform a superimposing processing for a B-mode image and a color Doppler image, a superimposing processing for a B-mode image and a power Doppler image, and in addition, for example, a composing processing for combining those images with data such as a name of the patient, a photographing data and the like entered through the control panel. However, those processings are not different from the conventional ones, and thus an illustration of those functions are omitted. Display image data representative of the composed images developed in the image composing unit 504 is fed to the observation television monitor 707 in which an image is displayed on a display screen.

Figure 3:
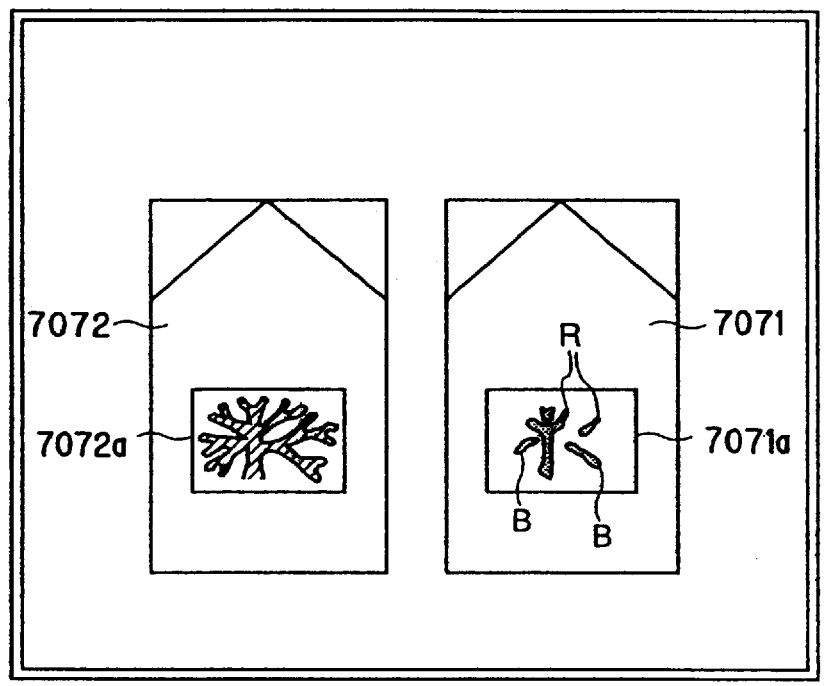
FIG. 3 is a typical illustration showing a characteristic display appearance for the ultrasonic diagnostic apparatus according to the embodiment of the present invention.

FIG. 3 is a typical illustration showing a characteristic display appearance for the ultrasonic diagnostic apparatus according to the embodiment of the present invention.

As shown in FIG. 3, the same two B-mode images 7071 and 7072 are displayed side by side on a display screen of the observation television monitor 707. A color Doppler image is superimposed on an area (ROI) 7071a of the B-mode image 7071 which is one of the two B-mode images 7071 and 7072. And a power Doppler image is superimposed on an area (ROI) 7072a of another B-mode images 7072 (the areas (ROI) on both the B-mode images are the same region).

In the color Doppler image displayed on the area (ROI) 7071a of the B-mode image 7071, a blood flow involved in a direction coming to the ultrasonic probe 20 (cf. FIG. 1), a blood flow involved in a direction going away from the ultrasonic probe, and a velocity of a blood flow are represented by red (R), blue (B) and luminance, respectively. On the other hand, in the power Doppler image displayed on the area (ROI) 7072a of the B-mode image 7072, a distribution of the power is indicated with a variation of color. Thus, when the color Doppler image and the power Doppler image are simultaneously displayed side by side, it is possible to find an existence site of a blood vessel through the power Doppler image, and to see a blood flow direction and a blood flow velocity of the blood vessel through the color Doppler image.

As mentioned above, when the color Doppler freeze selection button 7012 and the power Doppler freeze selection button 7013 on the control panel 701 are operated to switch the color Doppler freeze switch 501a and the power Doppler freeze switch 501b to the turn-on state, the color Doppler image of the dynamic picture image and the power Doppler image of the dynamic picture image are displayed within the area (ROI) 7071a and the area (ROI) 7072a shown in FIG. 3, respectively. And when the color Doppler freeze switch 501a and the power Doppler freeze switch 501b are switched to the turn-off state, the color Doppler image of the freeze image and the power Doppler image of the freeze image are displayed within the area (ROI) 7071a and the area (ROI) 7072a shown in FIG. 3, respectively. According to the present embodiment, since there are individually provided the color Doppler freeze selection button 7012 and the power Doppler freeze selection button 7013, the color Doppler image and the power Doppler image shown in FIG. 3 may be independently switched to the dynamic picture image and the freeze image.

Figure 4:
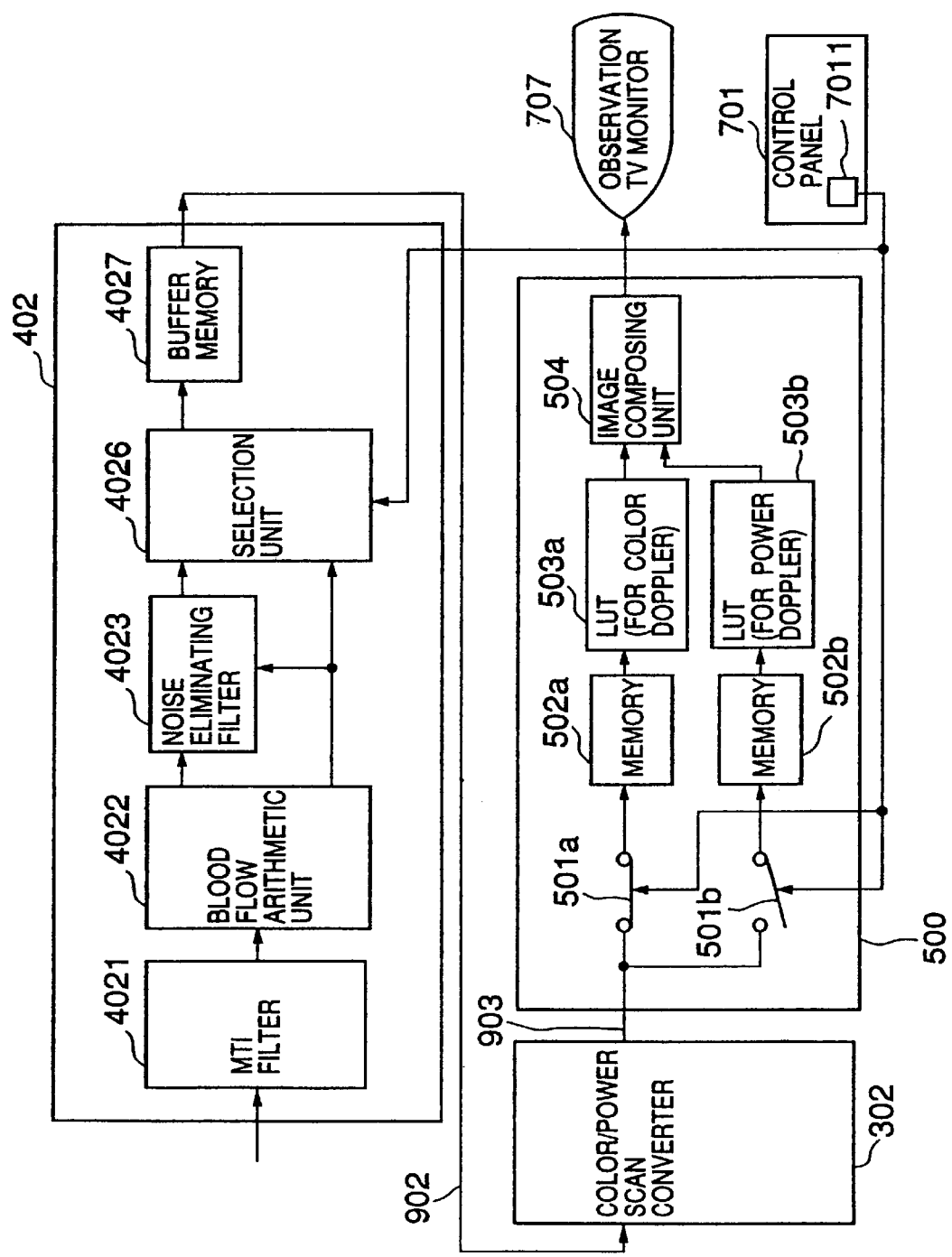
FIG. 4 is a detail block diagram of characteristic portions of the ultrasonic diagnostic apparatus according to another embodiment of the present invention.

FIG. 4 is a detail block diagram of characteristic portions of the ultrasonic diagnostic apparatus according to an alternative embodiment of the present invention. In FIG. 4, the same parts are denoted by the same reference numbers as those of FIG. 2, and the redundant description will be omitted.

The color Doppler data after passing through the noise eliminating filter 4023 and the power Doppler data outputted from the blood flow arithmetic unit 4022 are supplied to the selection unit 4026 in which any one of those data is selected in accordance with a mode selection control signal designated through an operation of the mode selection button 7011 provided on the control panel 701. The data thus selected is fed to the buffer memory 4027. In this manner, according to the present embodiment, any one of the color Doppler data and the power Doppler data is temporarily simply outputted from the selection unit 4026. This feature permits a half capacity of memory to be used as compared with the structure shown in FIG. 2. The data stored in the buffer memory 4027 is fed via the echo bus 902 to the color/power scan converter 302 and then to the display control unit 500.

According to the embodiment shown in FIG. 4, there is provided such an arrangement that the color Doppler freeze switch 501a and the power Doppler freeze switch 501b are switched on an interlocking basis in such a manner that when one of those switches is turned on, another is turned off. Those two switches are switched in cooperation with the mode selection by the mode selection button 7011 provided on the control panel 701. When the mode selection button 7011 is operated so that the color Doppler data is outputted from the selection unit 4026, the color Doppler freeze switch 501a is turned on and the power Doppler freeze switch 501b is turned off. On the other hand, when the mode selection button 7011 is operated so that the power Doppler data is outputted from the selection unit 4026, the color Doppler freeze switch 501a is turned off and the power Doppler freeze switch 501b is turned on. Consequently, with respect to the color Doppler image and the power Doppler image displayed on the display screen of the observation television monitor 707, always, one of those images is a dynamic image and another is a freeze image. At that time, the modes of ultrasonic transmission and reception by the transmit-receive unit 201 shown in FIG. 1 and the filter characteristics of MTI filter 4021 of the color/power Doppler analyzing unit 402, etc are switched to a mode suitable for obtaining an image involved in the dynamic image display, of the color Doppler image and the power Doppler image.

Incidentally, in case of the structure in which the color Doppler image and the power Doppler image can be independently frozen, as shown in FIG. 2, the modes of ultrasonic transmission and reception by the transmit-receive unit 201 and the filter characteristics of MTI filter 4021 of the color/power Doppler analyzing unit 402 are switched, when only one of those images is subjected to the dynamic image display, to a mode suitable for obtaining the image involved in the dynamic image display, but when both the color Doppler image and the power Doppler image are subjected to the dynamic image display, it is preferable that the modes of ultrasonic transmission and reception by the transmit-receive unit 201 and the filter characteristics of MTI filter 4021 are optionally switched between a mode which is optimal when both the images are integrated and a mode which is optimal for obtaining any one of those images. The reason why this is to do so is that even when both the images are subjected to the dynamic image display, it may happen that images of interest are either one of those images, and it may also happen that both the images are compared with each other.

It is to be noted that according to the present embodiment, while the color Doppler image and the power Doppler image are put side by side exactly on line, it is acceptable that two windows are set up, as the multi-window, at optional locations on a display screen, and the color Doppler image or the power Doppler image are displayed in the respective windows, or alternatively it is also acceptable that one of the color Doppler image and the power Doppler image, which is more interest as compared with another, is displayed with an enlargement and another with a reduction.

As described above, according to an ultrasonic diagnostic apparatus of the present invention, a color Doppler image and a power Doppler image are simultaneously displayed on a one display screen. This feature makes it possible to obtain a lot of blood flow information, thereby contributing to enhancement of a diagnostic ability of an ultrasonic diagnostic apparatus.

While the present invention has been described with reference to the particular illustrative embodiments, it is not to be restricted by those embodiments but only by the appended claims. It is to be appreciated that those skilled in the art can change or modify the embodiments without departing from the scope and spirit of the present invention.

I claim:

1. An ultrasonic diagnostic apparatus in which an ultrasonic pulse beam is transmitted into an organism and ultrasonic waves reflected within the organism are received to obtain received signals, this process is repeatedly performed to obtain the received signals, and an image is displayed in accordance with the received signals thus obtained, said ultrasonic diagnostic apparatus comprising:

a blood flow velocity arithmetic unit for extracting a Doppler transition component of the reflected ultrasonic waves in accordance with the received signals to evaluate a distribution of a velocity of a blood flow within the organism in accordance with the extracted Doppler transition component;

a blood flow power arithmetic unit for extracting a Doppler transition component of the reflected ultrasonic waves in accordance with the received signals to evaluate a distribution of a power of a blood flow within the organism in accordance with the extracted Doppler transition component; and an image display unit for simultaneously displaying on a display screen a first image representative of a blood flow velocity distribution evaluated by said blood flow velocity arithmetic unit, and a second image representative of a blood flow power distribution evaluated by said blood flow power arithmetic unit.

2. An ultrasonic diagnostic apparatus according to claim 1, wherein said ultrasonic diagnostic apparatus further comprises a display control unit adapted to provide, independently for said first image and said second image, a selective control between a dynamic image display mode in which a plurality of frames of images, which are sequentially generated, are sequentially transmitted to said image display unit so that the plurality of frames of images are sequentially displayed on the display screen, and a still image display mode in which a frame of image is kept on being displayed on the display screen.

3. An ultrasonic diagnostic apparatus according to claim 1, wherein said ultrasonic diagnostic apparatus further comprises a display control unit adapted to provide, for said first image and said second image, a selective control between a dynamic image display mode in which a plurality of frames of images, which are sequentially generated on one of said first image and said second image, are sequentially transmitted to said image display unit so that the plurality of frames of images are sequentially displayed on the display screen, and a still image display mode in which a frame of image, on another of said first image and said second image, is kept on being displayed on the display screen.

4. An ultrasonic diagnostic apparatus according to claim 1, wherein said ultrasonic diagnostic apparatus further comprises a map storage unit for storing a first map for defining an association between a blood flow velocity data representative of the blood flow velocity distribution and a display data representative of the first image displayed on the display screen of said image display unit, and a second map for defining an association between a blood flow power data representative of the blood flow power distribution and a display data representative of the second image displayed on the display screen of said image display unit, said second map being different from said first map.

* * * * *